United States Patent [19]

Ettinger et al.

[11] Patent Number: 5,275,165
[45] Date of Patent: Jan. 4, 1994

[54] MAGNETIC RESONANCE GUIDED ULTRASOUND THERAPY SYSTEM WITH INCLINED TRACK TO MOVE TRANSDUCERS IN A SMALL VERTICAL SPACE

[75] Inventors: Robert H. Ettinger; Harvey E. Cline, both of Schenectady; Ronald D. Watkins, Niskayuna; Kenneth W. Rohling, Burnt Hills, all of N.Y.

[73] Assignee: General Electric Company, Schenectady, N.Y.

[21] Appl. No.: 972,331

[22] Filed: Nov. 6, 1992

[51] Int. Cl.$^5$ .............................................. A61B 5/055
[52] U.S. Cl. ...................... 128/653.2; 128/24 AA; 607/96
[58] Field of Search .................. 128/653.2, 399, 736, 128/24; 324/315, 309

[56] References Cited

U.S. PATENT DOCUMENTS

| | | | |
|---|---|---|---|
| 4,914,608 | 4/1990 | LeBihan et al. | 364/557 |
| 4,951,688 | 8/1990 | Keren | 128/653.2 |
| 5,078,143 | 1/1992 | Okazaki et al. | 128/24 AA |
| 5,113,848 | 5/1992 | Krauss et al. | 128/24 EL |
| 5,131,392 | 7/1992 | Jolesz et al. | 128/653.2 |
| 5,207,214 | 5/1993 | Romano | 128/24 AA |

FOREIGN PATENT DOCUMENTS 2123963 2/1984 United Kingdom ............. 128/653.2

OTHER PUBLICATIONS

"Effects of Physical Parameters on High Temperature Ultrasound Hyperthermia Ultrasound" in Med. & Biol., vol. 16, No. 4, pp. 409-420, 1990.

*Primary Examiner*—Ruth S. Smith
*Attorney, Agent, or Firm*—Lawrence P. Zale; Marvin Snyder

[57] ABSTRACT

A magnetic resonance (MR) surgery system facilitates surgery with a focussed ultrasound transducer that selectively destroys tissue in a region within a subject. The focussed energy transducer dissipates energy at a focal point within the region of tissue to be destroyed. A non-magnetic positioning device having a vertical dimension small enough to fit easily within the bore of an MR magnet moves an energy transducer in a limited vertical space. The positioning device employs a plurality of hydraulic positioners and an inclined plane to position the ultrasound focal point under the control of an operator. An MR imaging system employing a temperature sensitive pulse sequence creates an image of the tissue and the region being heated to allow the operator to adjust the position of the ultrasonic transducer so as to direct ultrasonic energy to the appropriate location.

4 Claims, 5 Drawing Sheets

MAGNETIC RESONANCE GUIDED ULTRASOUND THERAPY SYSTEM WITH INCLINED TRACK TO MOVE TRANSDUCERS IN A SMALL VERTICAL SPACE

CROSS REFERENCE TO RELATED APPLICATIONS

This application is related to U.S. patent application Magnetic Resonance Surgery Using Heat Waves Produced With A Laser Fiber or Focussed Ultrasound by Harvey E. Cline and Thomas R. Anthony et al. Ser. No. 07/751,259 filed Aug. 29, 1991 and Magnetic Resonance Guided Focussed Ultrasound Surgery Ser. No. 07/854,040 filed Mar. 19, 1992 by Harvey Cline, Robert Ettinger, Kenneth Rohling, Ronald Watkins both assigned to the present assignee and hereby incorporated by reference.

BACKGROUND OF THE INVENTION

1. Field of the Invention

The present invention relates to a system for enabling surgery to be performed by vibrational heating and more particularly to a system for surgery by ultrasonic heating guided by magnetic resonance (MR) imaging.

2. Description of Related Art

Conventional Magnetic Resonance Imaging (MRI) provides the radiologist with internal views of a subject's anatomy. MRI provides excellent contrast between different tissues and is useful in planning surgical procedures. A tumor in a subject is much more visible in an MR image than as seen in actual surgery because the tumor and normal tissue often look similar in surgery. The tumor can also be obscured by blood during surgery. A view of the heated region is provided with the use of MR temperature sensitive pulse sequences. Known MR temperature sensitive pulse sequences are described in U.S. Pat. No. 4,914,608 Invivo Method for Determining and Imaging Temperature of an Object/Subject from Diffusion Coefficients Obtained by Nuclear Magnetic Resonance, Denis LeBihan, Jose Delannoy, and Ronald L. Levin issued Apr. 3, 1990. Experiments on animals show that a heated zone above a critical temperature destroys tissue. This zone increases in size with time as the heat is applied to reach a steady state of both temperature and heat flow. If the maximum temperature is limited to 100 deg. C, then the heated zone, the area exceeding a critical temperature causing destruction of tissue, approaches 1 centimeter in diameter. It is difficult to predict the heated zone geometry because the heat flow depends on the profusion of blood as well as the tissue thermal properties.

Tumors have been selectively destroyed in cancer subjects using focussed ultrasound heating in the absence of MR imaging at the University of Arizona, as reported by B. E. Billard, K. Hynynen and Robert B. Roemer Effects of Physical Parameters on High Temperature Ultrasound Hyperthermia Ultrasound in Med. & Biol. Vol. 16, No. 4, pp. 409–420, 1990 and hereby incorporated by reference. Billard et al. disclose that the control of heat is improved by using short heating pulses where the effect of blood perfusion is negligible. However, since they do not image the temperature distribution, it is difficult to hit small, deep laying targets.

It would be beneficial to be able to accurately localize heat to selectively kill or destroy tumor tissue without damage to surrounding healthy tissue.

OBJECTS OF THE INVENTION

It is an object of the present invention to position focussed ultrasound equipment in a limited vertical space guided by magnetic resonance imaging.

It is another object of the present invention to selectively destroy tumors with a small amount of invasiveness.

SUMMARY OF THE INVENTION

Pulsed heat from focussed ultrasound equipment is positioned to selectively destroy tumor tissue of a subject with minimal invasiveness by employing magnetic resonance (MR) imaging apparatus to provide, to an operator performing the procedure, images of a region within the subject being heated, such region including the tumor tissue. MR images are used to monitor the tissue temperature with a diffusion sensitive pulse sequence. A non-magnetic positioning means having a small vertical dimension is positioned within the bore of an MR magnet used for MR imaging. The ultrasound transducer is positioned by the positioning means such that it concentrates heat at a focal point on the tumor. The positioning means is responsive to a manually operated control unit and is constructed of non-magnetic positioners, such as hydraulic pistons which actuate structures to move the transducer. Since the positioning means must fit within the bore of a magnet used in MR imaging, it must have a small vertical elevation. This is accomplished by having positioners extend horizontally parallel with an inclined plane translating horizontal motion into vertical motion.

BRIEF DESCRIPTION OF THE DRAWINGS

The features of the invention believed to be novel are set forth with particularity in the appended claims. The invention itself, however, both as to organization and method of operation, together with further objects, may best be understood by reference to the following description taken in conjunction with the accompanying drawing in which:

DETAILED DESCRIPTION OF THE INVENTION

Tumor tissue in a subject can be selectively destroyed by localized heating without affecting the surrounding healthy tissue. In the present invention, heat is applied to the tumor tissue in a pulsed or oscillating fashion. This oscillation creates a heat wave at the focal point of the transducer. The pulsed heat is produced by an ultrasonic energy source driven in accordance with a sinusoidal component and a constant component, and thus varies sinusoidally. However, the constant heating from the heated focus point source steadily adds to the background thermal distribution.

For a further description of the pulsed heat distribution, refer to the aforementioned U.S. patent application Ser. No. 07/751,259, Cline, et al, filed Aug. 29, 1991.

Figure 1:
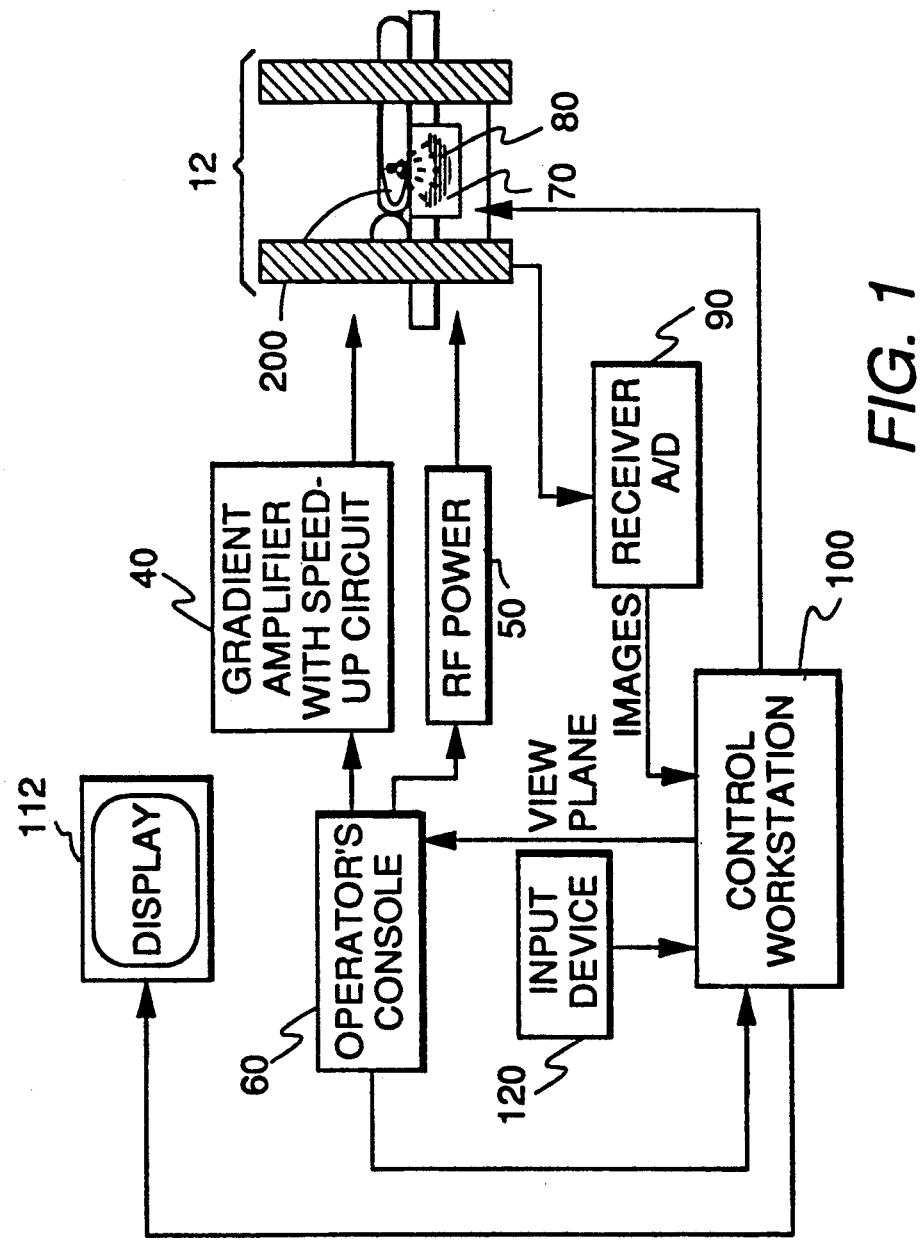
FIG. 1 is a schematic block diagram of a magnetic resonant pulsed heat system according to the present invention.

A schematic block diagram of the magnetic resonance surgery system according to the present invention is shown in FIG. 1. A magnetic resonant (MR) imaging system, 12 employs pulse sequences in the well known manner to rapidly acquire raw MR data used in constructing images of a subject 200. A gradient amplifier 40 and an rf power source 50 supply the power for the sequences. An operator console 60 is used to control the imaging system. The raw data is sent from receiver 90 to a control workstation 100 that displays display 112 to the operator. Control workstation 100 computes a path to a desired location within subject 200 from transducer 80 which avoids bone and air spaces. The operator indicates the desired location of the focal point of ultrasound transducer 80 by means of an input device 120 which can be a three-dimensional pointing device such as a track ball or a mouse. Control workstation 100 actuates positioning means 70 to position ultrasound transducer 80. Magnetic resonant imaging system 12 then employs pulse sequences to rapidly acquire temperature sensitive images of subject 200. Since both the internal structures and heated regions are imaged, the operator can accurately position the heated region to correspond to a desired internal structure through input device 120.

Figure 2:
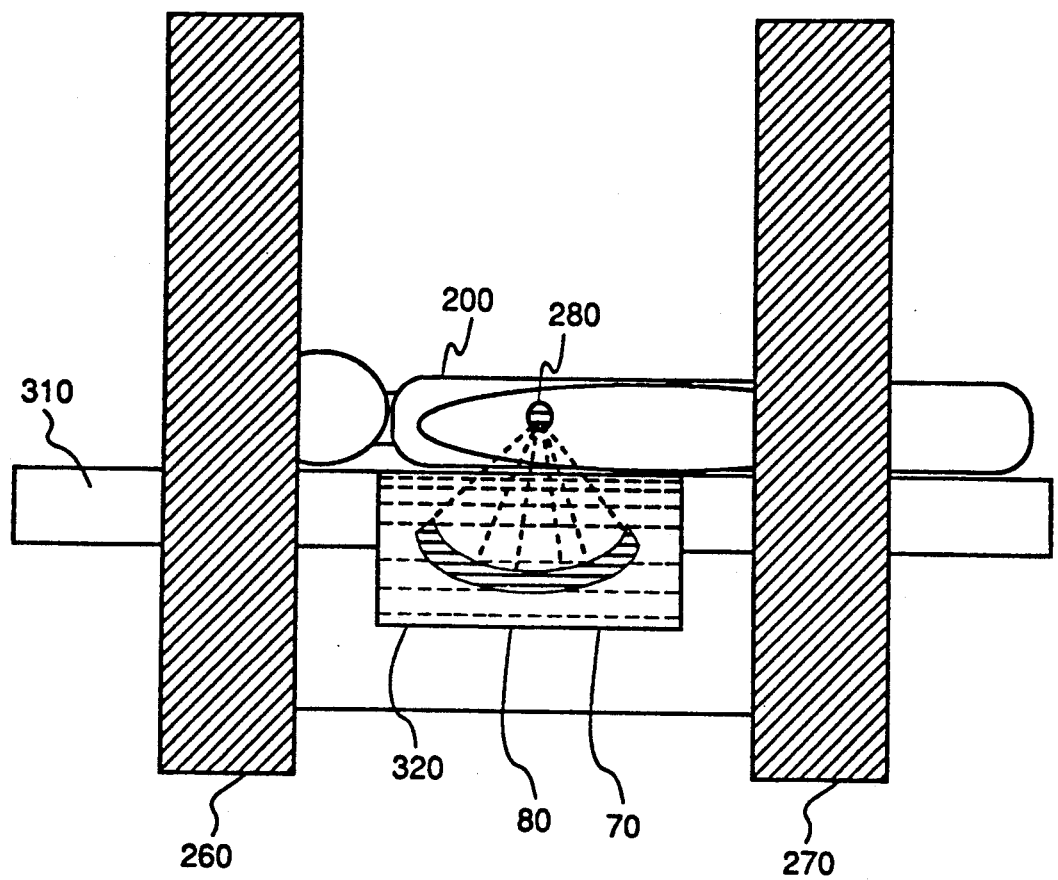
FIG. 2 is a diagrammatic illustration of a subject positioned for surgery within the bore of the magnets of an MRI system of FIG. 1.

As shown in FIG. 2, subject 200 is situated on a table 310 designed to accommodate a focussed ultrasound transducer 80 in an ultrasound conducting liquid 320. Ultrasound conducting liquid 320 chosen is one that will conduct ultrasonic energy with little attenuation. Ultrasound transducer 80 can be moved inside the bore of magnets 260, 270 by positioning means 70 to focus on different locations within subject 200. A path is computed by control workstation (100 of FIG. 1) from a set of images of the subject taken during surgery planning avoiding bone or air in the path of the ultrasound beam. The energy produced by ultrasound transducer 80 is aimed along the computed path by positioning means 70, focussed onto a tumor 280 and pulsed to selectively heat the tumor. The ultrasound transducer is moved while the operator views cross sectional temperature sensitive images.

Figure 3A:
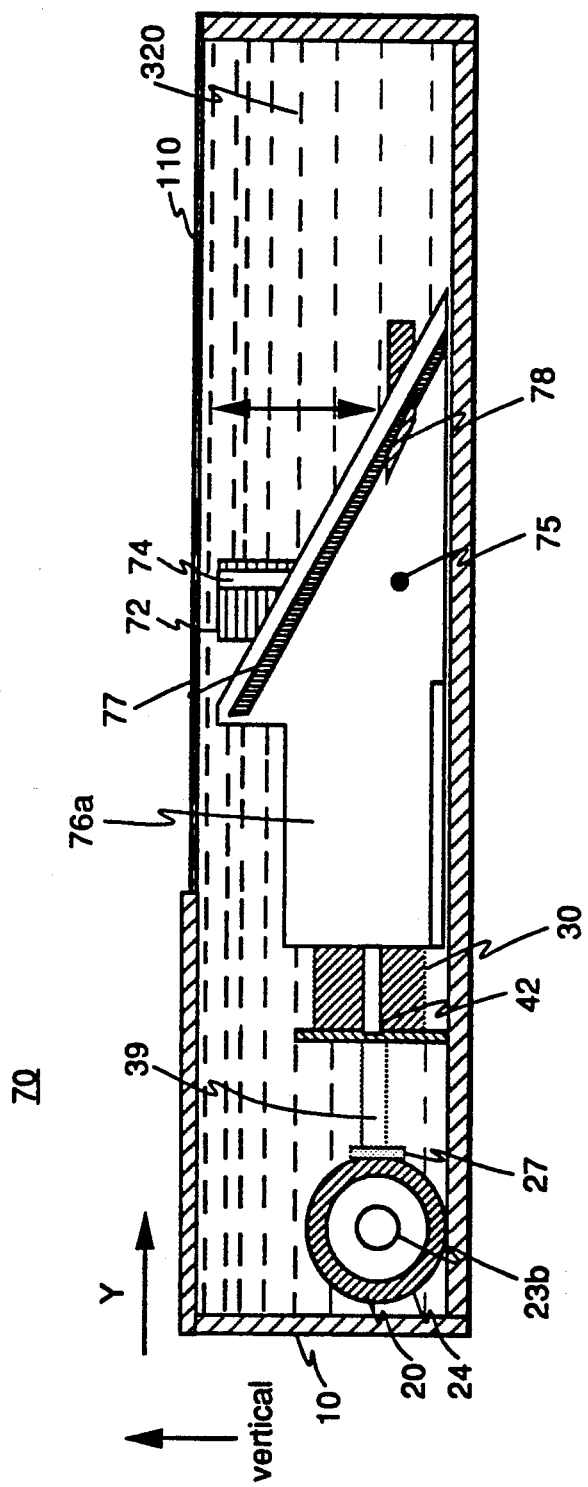
FIGS. 3a and 3b are sectional elevational and plan views, respectively of an embodiment of the non-magnetic positioning means of FIG. 1 or FIG. 2.
Figure 3B:
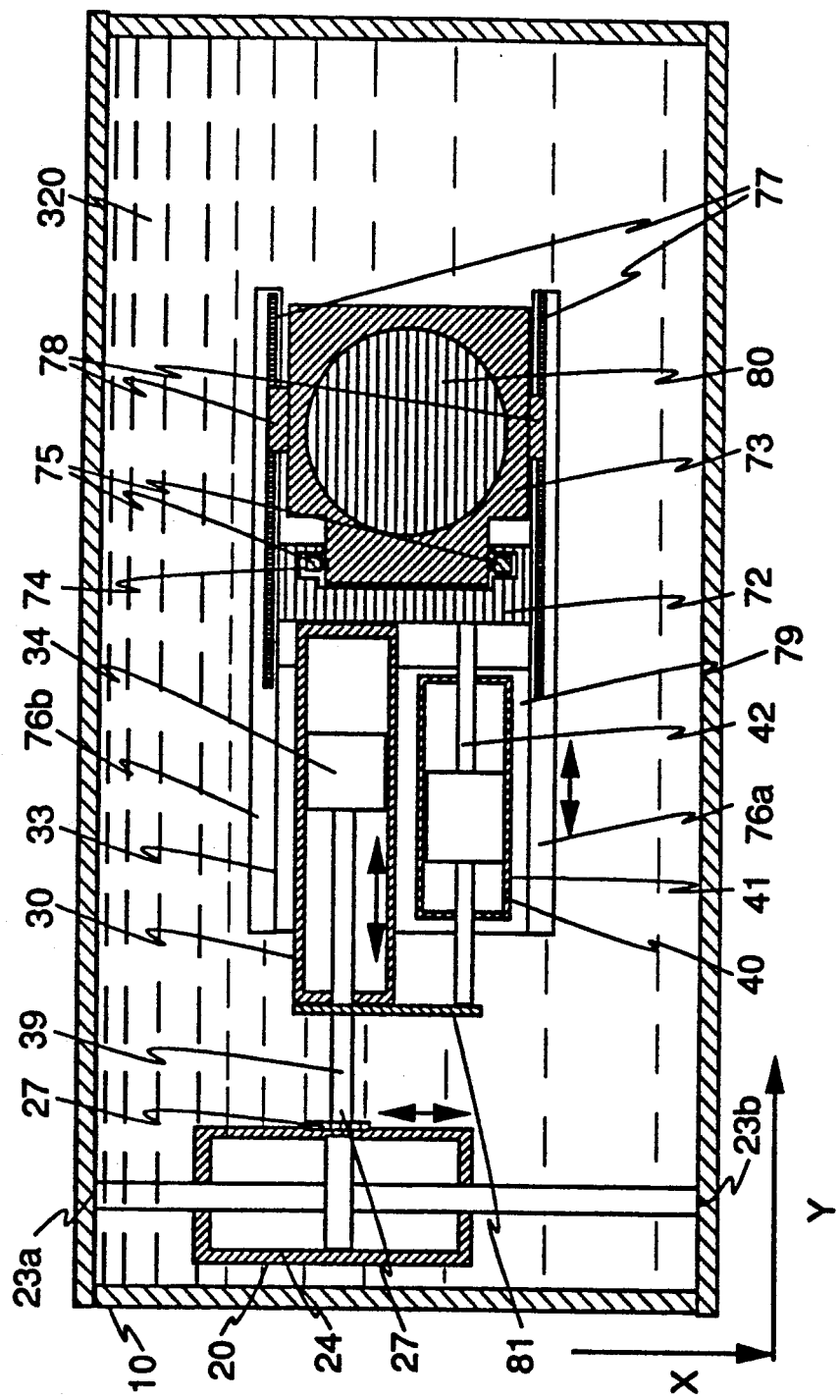

FIGS. 3a and 3b are a more detailed illustration of positioning means 70 of FIG. 2, FIG. 3a being an elevational view and FIG. 3b being a plan view of positioning means 70. All materials of positioning means 70 are non-metallic and non-magnetic in order to minimize any interference with the magnetic resonance imaging system. Positioning means 70 employs a casing 10 which encloses the ultrasound transmitting fluid 320, which is preferably water. An ultrasound membrane 110 comprised of a flexible material which is ultrasound transparent, such as a MYLAR plastic film diaphragm, (MYLAR is a trademark of the E.I. du Pont Nemours and Company, Wilmington, Del.), covers a portion of positioning means 70 above transducer 80. Ultrasound membrane 110 is made thin enough to conform to the contours of a subject. The subject is placed on ultrasound membrane 110 with ultrasonic conducting gel (not shown) extending between the ultrasound membrane and the subject. Energy from ultrasound transducer 80 passes through fluid 320, through ultrasound membrane 110, through the ultrasound gel between ultrasound membrane 110 and into the subject. In order to efficiently transfer the energy, there should be no intervening air spaces between transducer 80 and the subject.

A first positioner 20 having attachment points 23a and 23b affixed to casing 10 includes a housing 24, shown as a cylinder, which moves in an "X" direction when actuated, denoted as shown. Positioner 20, when actuated, causes motion of a structure 27. Positioners in the present embodiment are actuated by having fluid, such as hydraulic fluid, pumped to and from them by fluid lines. The fluid lines are not shown in FIGS. 3a and 3b for clarity, but are illustrated in subsequent figures.

Structure 27 is connected to a shaft 39 which is a part of a second positioner 30. Shaft 39 passes through a casing 33 and is connected to a piston 34. Casing 33 is affixed to vertical guide 72. Positioner 30, when actuated, causes vertical guide 72 to move in a "Y" direction relative to positioner 20, as shown. Vertical guide 72 has at least one vertical notch 74 which extends in a vertical direction.

A transducer plate 73 has a bearing on each side which slideably fits into vertical notch 74 guiding the transducer plate in a vertical direction. In an alternate embodiment, transducer plate has at least one tab (in this embodiment, a pair of tabs) 78 protruding from the plate. Tabs 78 of transducer plate 73 fit in vertical notches 74.

A vertical positioner 40 employs a casing 41, shown as a cylinder, and a piston-driven actuation shaft 42. Casing 41 is affixed to a junction piece 79 which is connected to at least one inclined guide, in this embodiment, two inclined guides 76a and 76b are used. The inclined guides each have an inclined groove 77 which decreases in vertical height along the positive "Y" direction. Actuation shaft 42 is connected to vertical guide 72, passes through casing 41 and is affixed to anchor plate 81. Anchor plate 81 is also affixed to casing 33 of second positioner 30. A piston 43 fitting snugly inside casing 41 is fixed to actuation shaft 42. Vertical positioner 40, when actuated, causes a motion of casing 41, junction piece 79, inclined guides 76a and 76b in the "Y" relative to vertical guide 72 and anchor plate 81. Bearings 75 in vertical notches 74 limit motion in the "Y" direction, thereby rendering transducer plate 73 substantially fixed in the "Y" direction relative to vertical guide 72. As inclined guides 76a and 76b move in the "Y" direction, tabs 78 ride along inclined grooves 77 causing transducer plate 73 to move in a vertical direction. Ultrasound transducer 80, fixed to transducer plate 73, may therefore be positioned in the "X", "Y" and vertical directions by positioning means 70.

The present embodiment employs tabs, notches, grooves and bearings to slideably attach the moving elements of the invention, but many conventional methods of attachment resulting in similar motion are equally acceptable in alternative embodiments.

Figure 4:
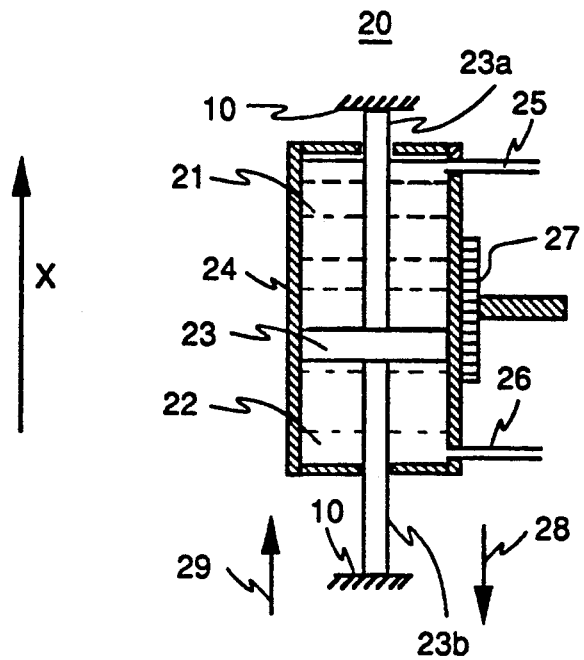
FIG. 4 is a sectional illustration of a first positioner according to the present invention.

FIG. 4 is a cut-away illustration of positioner 20 having a cylindrical housing 24 in which is fitted a piston 23. Piston 23 creates a fluid-tight seal between itself and housing 24, defining two chambers 21 and 22. Piston 23 has two extensions, 23a and 23b, which are secured to casing 10 of the positioning means shown in FIGS. 3a and 3b. Hydraulic fluid is pumped into chamber 21 through hydraulic line 35, causing housing 24 to move in the direction marked by arrow 29. This causes fluid in chamber 22 to exit through hydraulic line 26. Conversely, when fluid is pumped in through hydraulic line 26 into chamber 22, housing 24 moves in the X direction marked by arrow 28, causing fluid in chamber 21 to exit through hydraulic line 25. Structure 27 is affixed to housing 24 and moves in the same direction as housing 24.

Figure 5:
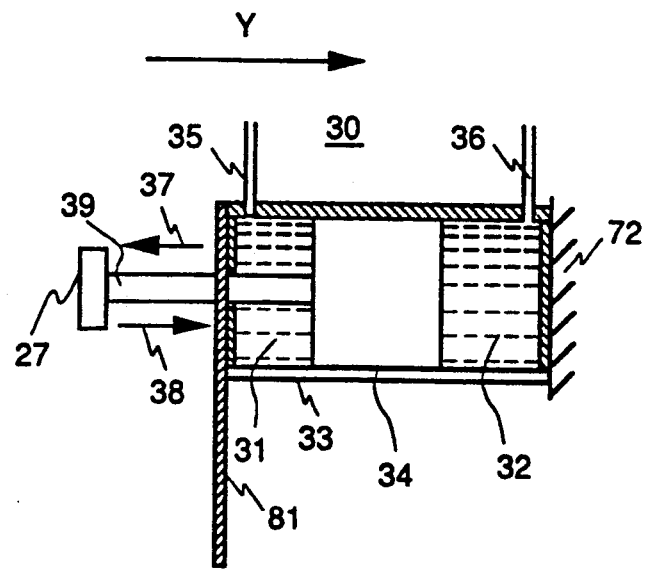
FIG. 5 is a sectional illustration of a second positioner according to the present invention.

FIG. 5 is a sectional illustration of positioner 30 of FIGS. 3a and 3b. Positioner 30 has a cylindrical housing 33 which encloses piston 34, creating chambers 31 and 32. Structure 27 is affixed to casing 24 of positioner 20 of FIGS. 3a, 3b and 4, and also to actuation shaft 39 of second positioner 30. Casing 33 is affixed to vertical guide 72 of FIGS. 3a and 3b. As hydraulic fluid enters through hydraulic line 35, casing 33 and vertical guide 72 move in the "Y" direction marked by arrow 37. When hydraulic fluid enters chamber 32 through hydraulic line 36, hydraulic fluid exits chamber 31 through hydraulic line 35 causing motion of casing 33 and vertical guide 72 in the "Y" direction marked by arrow 38.

Figure 6:
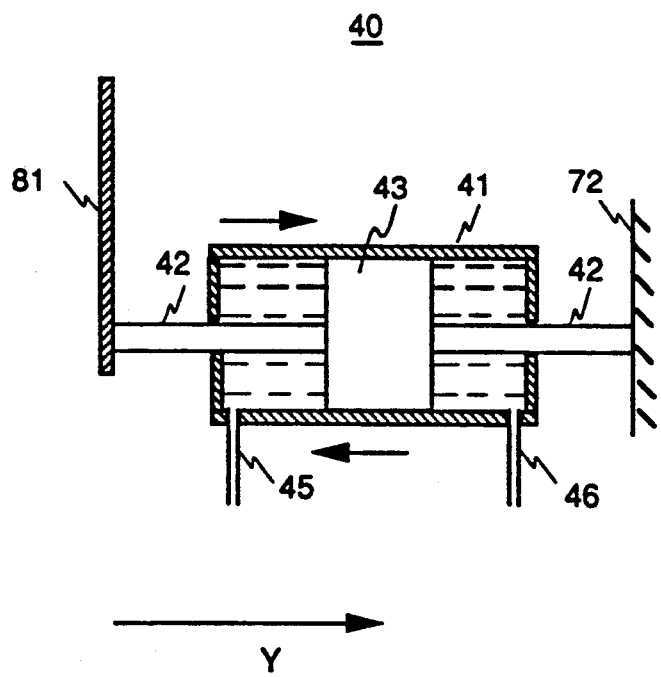
FIG. 6 is a sectional illustration of a vertical positioner according to the present invention.

FIG. 6 is a cutaway view of positioner 40 of FIG. 3. The functioning of this positioner is very similar to that of first positioner 20 of FIGS. 3a, 3b and 4. Actuator shaft 42 is affixed at a first end to anchor plate 81 and at a second end to vertical guide 72. Casing 41 is attached to junction piece (79 of FIG. 3b) which is turn connected to inclined guides (76a & 76b of FIG. 3b). A piston 43, affixed to actuator shaft 42, creates a fluid-tight seal with casing 41. Fluid is pumped through lines 45 and 46 causing casing 41, and hence inclined guides, to move in the "Y" direction relative to anchor plate 81 and vertical guide 72.

The motion of the first, second and vertical positioners cause motion in three dimensions of transducer plate having an ultrasound transducer attached to it, thereby allowing positioning of the ultrasound transducer to focus on a desired point within the subject.

While several presently preferred embodiments of the invention have been described in detail herein, many modifications and variations will now become apparent to those skilled in the art. It is, therefore, to be understood that the appended claims are intended to cover all such modifications and variations as fall within the true spirit of the invention.

What is claimed is:

1. A magnetic resonance pulsed heat system for selectively heating a region of a subject, comprising:
   a) a magnetic resonance (MR) imaging means for imaging internal structures of said subject and for creating temperature sensitive images of such structures during surgery, the MR imaging means having a table for holding said subject:
   b) an energy transducer for focussing vibrational energy to create a heated region within the subject;
   c) an ultrasonic energy conductive interface adapted to be placed between said subject and the energy transducer;
   d) non-magnetic positioning means for moving the energy transducer, relative to the table, in a limited vertical space for positioning the heated region, the positioning means comprising:
      1) a frame attached to the table;
      2) a positioner having a first fixation shaft attached to the frame, and a housing fixed with reference to an anchor plate, the anchor plate being movable in a first direction relative to the fixation shaft,
      3) a vertical guide extending in a vertical direction,
      4) a transducer plate to which the transducer is connected is slideably connected to the vertical guide to allow motion in a vertical direction,
      5) a second positioner connected to the anchor plate, and to the vertical guide, the second positioner being adapted to cause motion of the vertical guide and transducer plate in a second direction relative to the first positioner,
      6) an inclined guide having at least one inclined edge oriented in a vertical direction, the inclined edge slideably connected to the transducer plate, and
      7) a third positioner having a first fixation shaft connected to the inclined guide and a second fixation shaft connected to the anchor plate for causing the inclined guide to move relative to the vertical guide such that the transducer slideably moves along the inclined edge of the inclined guide in a vertical direction;
   e) control means for receiving from an operator, location information regarding a desired position of the heated region relative to said internal structures, information regarding actual position of the heated region relative to said internal structures, and causing the positioning means to move the transducer such that the heated region is positioned at the desired position; and
   f) display means for displaying the internal structures and temperature sensitive images from the MR imaging means to the operator to enable the operator to control the position and size of the heated region.

2. The magnetic resonance pulsed heat system of claim 1 wherein each positioner comprises:
   a) a casing;
   b) a piston fitted in the casing;
   c) at least one piston chamber between the casing and the piston; and
   d) at least one lead tube connected to the chamber.

3. The magnetic resonance pulsed heat system of claim 1 wherein the vibrational energy transducer comprises an ultrasound transducer, and the ultrasonic energy conductive interface comprises:
   a) an ultrasound transparent membrane adapted to be in contact with said subject;
   b) an ultrasound transparent medium in contact with the membrane and situated between the membrane and the transducer, for conducting ultrasound energy from the transducer to the membrane.

4. The magnetic resonance pulsed heat system of claim 1 wherein the control means comprises:
   a) input means for allowing the operator to choose a three-dimensional position for said transducer; and
   b) control workstation means for converting the chosen three-dimensional position to a position signal for driving the positioning means, the control workstation means being coupled to the input means and the positioning means.

* * * * *